(12) United States Patent
Morgan et al.

(10) Patent No.: US 8,518,391 B1
(45) Date of Patent: Aug. 27, 2013

(54) MONOCYTES AS A GENE DELIVERY VECTOR FOR SECRETED PROTEINS TO TREAT ALZHEIMER'S DISEASE

(75) Inventors: Dave Morgan, Clearwater, FL (US); Siddharth G. Kamath, Tampa, FL (US); Lori Lebson, Baltimore, MD (US)

(73) Assignee: University of South Florida, Tampa, FL (US)

( * ) Notice: Subject to any disclaimer, the term of this patent is extended or adjusted under 35 U.S.C. 154(b) by 78 days.

(21) Appl. No.: 12/610,815

(22) Filed: Nov. 2, 2009

Related U.S. Application Data

(60) Provisional application No. 61/110,095, filed on Oct. 31, 2008.

(51) Int. Cl.
*A61K 48/00* (2006.01)
*C12N 5/078* (2010.01)

(52) U.S. Cl.
USPC .................................. 424/93.21; 424/93.71

(58) Field of Classification Search
USPC ........................................... 424/93.21, 93.71
See application file for complete search history.

(56) References Cited

U.S. PATENT DOCUMENTS

2008/0317732 A1* 12/2008 Hersh et al. ................. 424/94.63

OTHER PUBLICATIONS

Hemming et al. (2007) PLOS Medicine, vol. 4(8), 1405-1416.*
Malm et al. (2005) Neurobiology of Disease, vol. 18, 134-142.*
Serbina et al. (2006) Nature Immunol., vol. 7(3), 311-317.*
Goyert et al. (1988) Science, vol. 239(4839), 497-500.*
Webster, et al., Complement Component C1q Modulates the Phagocytosis of ABeta by Microglia, Experimental Neurology, 2000, vol. 161, pp. 127-138.
Paresce, et al., Microglial Cells Internalize Aggregates of the Alzheimer's Disease Amyloid Beta-Protein Via a Scavenger Receptor, Neuron, 1996, vol. 17, pp. 553-565.
Akiyama, et al., Inflammation and Alzheimer's Disease, Neurobiology of Aging, 2000, vol. 21, pp. 383-421.
Morgan, et al., Dynamic Complexity of the Microglial Activation Response in Transgenic Models of Amyloid Deposition: Implications for Alzheimer Therapeutics, J Neuropathol Exp Neurol, 2005, vol. 64, No. 9, pp. 743-753.
Wyss-Coray, Inflammation in Alzheimer Disease: Driving Force, Bystander or Beneficial Response?, Nature Medicine, 2006, vol. 12, No. 9, pp. 1005-1015.
Ladeby, et al., Microglial Cell Population Dynamics in the Injured Adult Central Nervous System, Brain Research Reviews, 2005, vol. 48, pp. 196-206.
Town, et al., Blocking TGF-Beta-Smad2/3 Innate Immune Signaling Mitigates Alzheimer-Like Pathology, Nature Medicine, 2008, vol. 14, No. 6, pp. 681-687.
Takata, et al., Microglial Transplantation Increases Amyloid-Beta Clearance in Alzheimer Model Rats, FEBS Letters, 2007, vol. 581, pp. 475-478.
Khoury, et al., Ccr2 Deficiency Impairs Microglial Accumulation and Accelerates Progression of Alzheimer-Like Disease, Nature Medicine, 2007, vol. 13, No. 4, pp. 432-438.
Simard, et al., Bone Marrow-Derived Microglia Play a Critical Role in Restricting Senile Plaque Formation in Alzheimer's Disease, Neuron, 2006, vol. 49, pp. 489-502.
Stalder, et al., Invasion of Hematopoietic Cells Into the Brain of Amyloid Precursor Protein Transgenic Mice, The Journal of Neuroscience, 2005, vol. 25, No. 48, pp. 11125-11132.
Malm, et al., Bone-Marrow-Derived Cells Contribute to the Recruitment of Microglial Cells in Response to Beta-Amyloid Deposition in APP/PS1 Double Transgenic Alzheimer Mice, Neurobiology of Disease, 2005, vol. 18, pp. 134-142.
Carty, et al., Adeno-Associated Viral (AAV) Serotype 5 Vector Mediated Gene Delivery of Endothelin-Converting Enzyme Reduces ABeta Deposits in APP + PS1 Transgenic Mice, Molecular Therapy, 2008, vol. 16, No. 9, pp. 1580-1586.
Burger, et al., Systemic Mannitol-Induced Hyperosmolality Amplifies rAAV2-Mediated Striatal Transduction to a Greater Extent Than Local Co-Infusion, Molecular Therapy, 2005, vol. 11, No. 2, pp. 327-331.
Iwata, et al., Identification of the Major ABeta1-42-Degrading Catabolic Pathway in Brain Parenchyma: Suppression Leads to Biochemical and Pathological Deposition, Nature Medicine, 2000, vol. 6, No. 2, pp. 143-150.
Imai, et al., Exogenous Microglia Enter the Brain and Migrate Into Ischaemic Hippocampal Lesions, Neuroscience Letters, 1999, vol. 272, pp. 127-130.
Cearley, et al., Transduction Characteristics of Adeno-Associated Virus Vectors Expressing Cap Serotypes 7, 8, 9, and Rh10 in the Mouse Brain, Molecular Therapy, 2006, vol. 13, No. 3, pp. 528-537.
Krauze, et al., Reflux-Free Cannula for Convection-Enhanced High-Speed Delivery of Therapeutic Agents, J. Neurosurg., 2005, vol. 103, pp. 923-929.
Ajami, et al., Local Self-Renewal can Sustain CNS Microglia Maintenance and Function Throughout Adult Life, Nature Neuroscience, 2007, vol. 10, No. 12, pp. 1538-1543.
Mildner, et al., Microglia in the Adult Brain Arise From Ly-6ChiCCR2+ Monocytes Only Under Defined Host Conditions, Nature Neuroscience, 2007, vol. 10, No. 12, pp. 1544-1553.
Gordon, et al., Exaggerated Astrocyte Reactivity After Nigrostriatal Deafferentation in the Aged Rat, The Journal of Comparative Neurology, 1997, vol. 388, pp. 106-119.
Holcomb, et al., Accelerated Alzheimer-Type Phenotype in Transgenic Mice Carrying Both Mutant Amyloid Precursor Protein and Presenilin 1 Transgenes, Nature Medicine, 1998, vol. 4, No. 1, pp. 97-100.

(Continued)

*Primary Examiner* — Anne Marie S Wehbe
(74) *Attorney, Agent, or Firm* — Nilay J. Choksi; Smith & Hopen, P.A.

(57) ABSTRACT

Disclosed is a method for the treatment of a neurodegenerative disorder by isolating a plurality of monocytic cells and introducing a vector containing a gene that expresses a protease capable of degrading amyloid peptide into the isolated monocytic cells. The modified cells are then administered to the patient. Preferably the introduced gene is selected from the group consisting of neprilysin, insulin degrading enzyme and endothelin converting enzyme. The protease capable of degrading amyloid peptide is secreted from the monocytic cells into the extracellular space thereof. According to one variant, the gene that expresses a protease capable of degrading amyloid peptide is the NEP gene with a deletion in the membrane binding domain and/or an appended signal peptide to drive secretion of the modified gene product. This invention contemplates the use of heterologous and autologos (the monocytic cells are obtained from the patient) transplants.

16 Claims, 4 Drawing Sheets

(56) References Cited

OTHER PUBLICATIONS

Best, et al., The Novel Gamma Secretase Inhibitor N-[cis-4-[(4-Chlorophenyl)Sulfonyl]-4-(2,5-Difluorophenyl) Cyclohexyl]-1, 1, 1-Trifluoromethanesulfonamide (MRK-560) Reduces Amyloid Plaque Deposition Without Evidence of Notch-Related Pathology in the Tg2576 Mouse, The Journal of Pharmacology and Experimental Therapeutics, 2007, vol. 320, No. 2, pp. 552-558.

Gordon, et al., Time Course of the Development of Alzheimer-Like Pathology in the Doubly Transgenic PS1 + APP Mouse, Experimental Neurology, 2002, vol. 173, pp. 183-195.

Leissring, et al., Enhanced Proteolysis of Beta-Amyloid in APP Transgenic Mice Prevents Plaque Formation, Secondary Pathology, and Premature Death, Neuron, 2003, vol. 40, pp. 1087-1093.

Marr, et al., Neprilysin Gene Transfer Reduces Human Amyloid Pathology in Transgenic Mice, The Journal of Neuroscience, 2003, vol. 23, No. 6, pp. 1992-1996.

Hsiao, et al., Correlative Memory Deficits, ABeta Elevation, and Amyloid Plaques in Transgenic Mice, Science, 1996, vol. 274, pp. 99-102.

Hemming, et al., Reducing Amyloid Plaque Burden via Ex Vivo Gene Delivery of an ABeta-Degrading Protease: A Novel Therapeutic Approach to Alzheimer Disease, PLOS Medicine, 2007, vol. 4, Issue 8, pp. 1405-1416.

West, et al., Unbiased Stereological Estimation of the Total Number of Neurons in the Subdivisions of the Rat Hippocampus Using the Optical Fractionator, The Anatomical Record, 1991, vol. 231, pp. 482-497.

Duff, et al., Increased Amyloid-Beta42(43) in Brains of Mice Expressing Mutant Presenilin 1, Nature, 1996, vol. 383, pp. 710-713.

* cited by examiner

MONOCYTES AS A GENE DELIVERY VECTOR FOR SECRETED PROTEINS TO TREAT ALZHEIMER'S DISEASE

CROSS REFERENCE TO RELATED APPLICATIONS

This application is a Non-Provisional Application of U.S. Provisional Application No. 61/110,095, filed Oct. 31, 2008, which is incorporated herein by reference.

STATEMENT OF GOVERNMENT INTEREST

This invention was made with Government support under Grant Nos. AG 25509 and AG 14590 awarded by the National Institutes of Health. The Government has certain rights in the invention.

FIELD OF INVENTION

This invention relates to gene therapy. More specifically, this invention relates to the treatment of Alzheimer's disease using monocytes as a gene delivery vector for the delivery of secreted proteins.

BACKGROUND OF THE INVENTION

The role of microglia/macropahages in the amyloid pathology of Alzheimer's Disease (AD) is an area of intense investigation. While inflammation associated with the amyloid deposits in AD brain may contribute to the pathogenesis of the disease (H. Akiyama et al., 2000), macrophages in vitro avidly digest amyloid fibrils (D. M. Paresce et al., 1996; S. D. Webster et al., 2000). A number of recent studies present evidence that grafted monocytes home to plaques in mouse models of amyloid deposition (T. M. Malm et al., 2005; A. K. Stalder et al., 2005) and can restrict amyloid deposition, most probably by phagocytosis and digestion of amyloid fibrils (A. R. Simard et al., 2006; J. El Khoury et al., 2007; K. Takata et al., 2007; T. Town et al., 2008).

However, it has been argued that studies labeling CNS infiltrating monocytes with bone marrow grafts may be confounded by CNS damage produced by the irradiation used to deplete the recipients bone marrow (R. Ladeby et al., 2005; B. Ajami et al., 2007; A. Mildner et al., 2007). This method of labeling circulating monocytes with grafted donor bone marrow may, thus, exaggerate the true extent of monocyte infiltration.

A separate issue is the challenging problem of exploiting gene therapy to treat neurodegenerative disorders such as Alzheimer's disease. Even using advanced methods such as convection enhanced delivery, it is rare that a gene therapy vector can transfect the entire cerebral cortex of a mouse, a region $\frac{1}{3000}^{th}$ the size of the human cortex (C. Burger et al., 2005; M. T. Krauze et al., 2005; C. N. Cearley and J. H. Wolfe, 2006; N. C. Carty et al., 2008). For almost a decade, the potential use of circulating monocytes which home to sites of CNS pathology has been proposed to overcome this gene delivery problem (F. Imai et al., 1999). However, to date the utility of this approach has not been demonstrated.

A major limitation to gene therapy for brain disorders involves the restricted distribution of gene delivery vectors following intracranial administration In addition, a central question in neuroimmunology concerns the extent to which blood borne monocytes migrate to the CNS in degenerative disorders. Therefore, what is needed is a method whereby circulating monocytes home to amyloid plaques in the brain and can be used as effective gene therapy vectors.

SUMMARY OF THE INVENTION

As shown herein, monocytes isolated from green fluorescent protein (GFP) expressing donors were transferred to amyloid-depositing transgenic mice by intravenous infusion. These monocytes spontaneously homed to compacted amyloid plaques in the brain. Twice weekly infusions of monocytes transfected with a genetically engineered form of the protease neprilysin completely arrested amyloid deposition. These data confirm monocyte migration to brain amyloid plaques in the absence of irradiation and demonstrate a novel method for therapeutic gene delivery to the CNS.

In a first embodiment, the invention includes a method for the treatment of Alzheimer's disease comprising the steps of isolating a plurality of monocytic cells and introducing a vector containing a gene that expresses a protease capable of degrading amyloid peptide into the isolated monocytic cells. The modified cells are then administered to the patient. Preferably the introduced gene is selected from the group consisting of neprilysin, insulin degrading enzyme and endothelin converting enzyme. The protease capable of degrading amyloid peptide is secreted from the monocytic cells into the extracellular space thereof. According to one variant of this embodiment, the gene that expresses a protease capable of degrading amyloid peptide is the NEP gene with a deletion in the membrane binding domain and/or an appended signal peptide to drive secretion of the modified gene product. This embodiment contemplates the use of heterologous and autologous (the monocytic cells are obtained from the patient) transplants.

A second embodiment includes method of testing the efficacy of a therapeutic gene for the treatment of neurodegenerative disease, comprising isolating a plurality of monocytic cells, introducing a vector containing a therapeutic gene of into the isolated monocytic cells, administering the monocytic cells into a subject, detecting the presence of the monocytic cells at the loci of neurodegeneration and/or determining the therapeutic effect of the product of the therapeutic gene of interest at the loci of neurodegeneration.

In a specific embodiment, the invention includes a method of administering Cd11b+ monocytic cells for brain repairs. The Cd11b+ cells a substantially contemporaneously prepared for grafting without placing them on any cell culture flask. This methods utilizes the migration of these cells across the blood brain barrier for homing to the specific sites in the brain where the brain damage is present. Although neprilysin is one of several different protease capable of degrading amyloid beta, any of these proteases can be used in this application, as long as active secreted forms of the enzymes are constructed.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
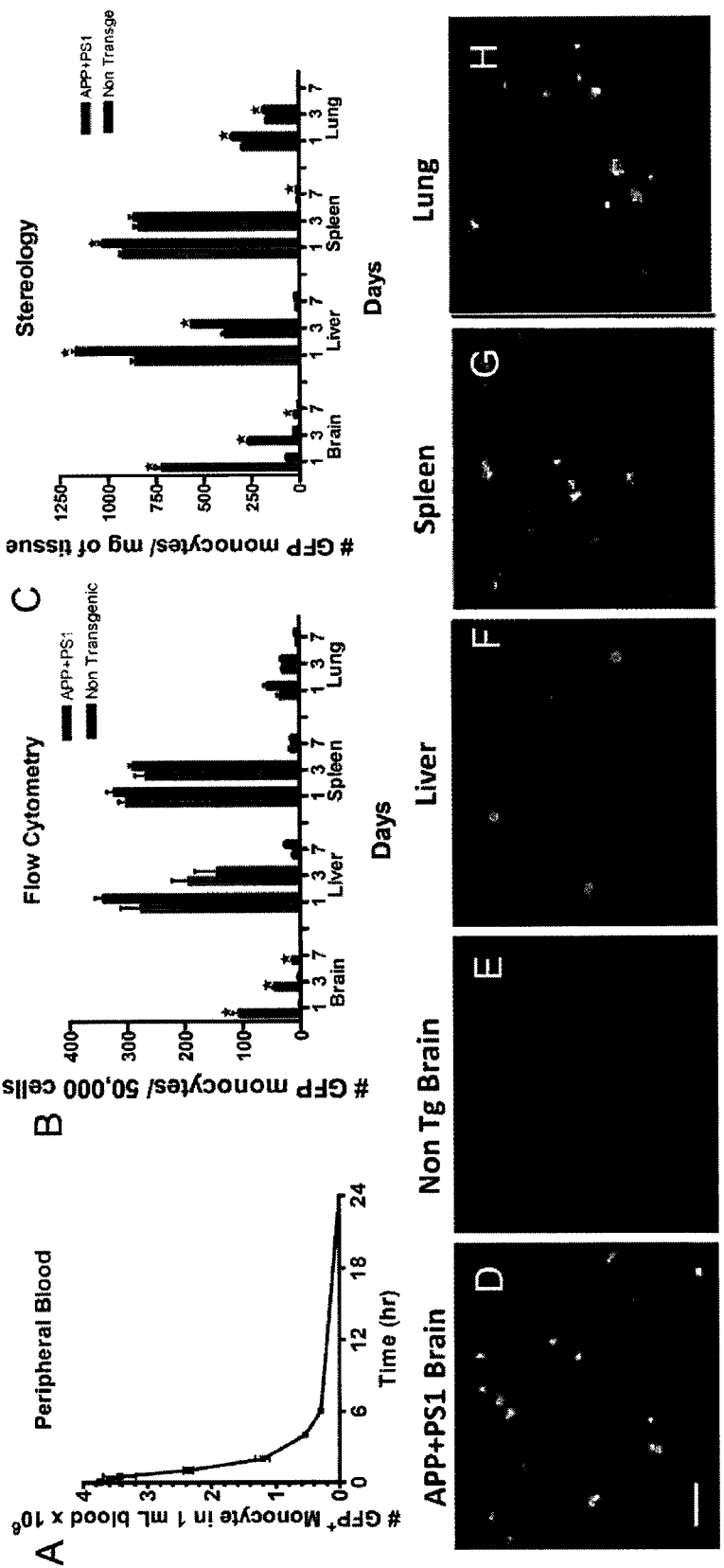
FIG. 1 shows that amyloid pathology increases the migration of infused GFP monocytes into brain. In panel A, single injection of $5 \times 10^6$ GFP bone marrow monocytes were injected into the left ventricle of the heart of nontransgenic mice. At the indicated time points, mice blood was collected and the number of GFP monocytes in the blood was measured by flow cytometry (n=4 at each time point). In panels B and C, mice were infused with $5 \times 10^6$ GFP+bone marrow monocytes into the left ventricle of the heart and organs were collected 1, 3 or 7 days following the injection. The organs were bisected and the number of monocytes present in each organ was quantified using flow cytometry (panel B) or stereology (panel C). n=4 for each organ. Panels D-H are representative micrographs f GFP staining in the tissues indicated above each panel. * P<0.05 by t-test. Scale bar=25 µm.

A central question in neuroimmunology concerns the extent to which blood borne monocytes migrate to the CNS in degenerative disorders. A major limitation to gene therapy for the brain disorders involves the restricted distribution of gene delivery vectors following intracranial administration. Here, the inventors isolated monocytes from green fluorescent protein (GFP) expressing donors and transferred to amyloid-depositing transgenic mice by intravenous infusion spontaneously homed to compacted amyloid plaques in the brain. Twice weekly infusions of monocytes transfected with a genetically engineered form of neprilysin, completely arrested amyloid deposition. These data confirm monocyte migration to brain amyloid plaques in the absence of irradiation and demonstrate a novel method for therapeutic gene delivery to the CNS.

The invention, therefore, includes a method of ex vivo gene therapy with multiple applications as well as demonstrating proof of concept for specific therapeutic genes in human conditions. In one embodiment, for example, of human gene therapy; a patient's own monocytes are elutriated from blood, transfected ex vivo, then reintroduced in a single visit. Given the short half lives of the monocytes, this may require repeated injections before therapeutic effects are observed. However, this self-limiting property would minimize the risk of unforeseen adverse effects that would be difficult to treat using more permanent gene therapy approaches.

For neurodegenerative disorders, this approach would permit distribution of the therapeutic gene throughout the brain, and deliver the gene precisely at locations undergoing degeneration. Compared to viral vectors, there would be no expression of the gene in unintended cells, or a gradient of expression around the injection site. Moreover, there would be no need for intracranial surgery, the hazards of which were evident in the first gene therapy trial for Alzheimer's disease (M. H. Tuszynski et al., 2005). The absence of integration into the host genome, and the use of postmitotic cells would diminish the risk for inadvertent transformation into oncogenic cells. Once the efficacy and safety of a given gene therapy approach is demonstrated using monocytes, the gene could be transfected into bone marrow stem cells which, with appropriate promoters to drive expression of the gene in infiltrating monocytes, and conceivably effect a permanent treatment for the disease.

Treatment of Neurodegenerative Diseases

Microglia and macrophages function to protect the nervous system by serving as debris scavengers and regulators of immune responses. Studies implicating the homing of monocytes to regions of CNS damage have led to the idea that these cells could be used to deliver therapeutic genes to the brain in Alzheimer's disease. Several Aβ degrading proteases have been identified by their ability to cleave Aβ; however, only Neprilysin, Insulin Degrading Enzyme and Endothelin Converting Enzyme have been reported to affect Aβ levels in the brains of experimental animal models.

Recent in vitro and in vivo studies demonstrate that the up regulation of Aβ degrading enzymes can significantly reduce the development of the Aβ peptide. Identification of a method to selectively upregulate brain neprilysin activity may provide a new therapeutic potential. To study the effects of neprilysin transfected monocytes on Aβ, the inventors utilized bone marrow harvested aseptically from 8-10 month old C57BL/6-Tg (ACTbGFP) mice that express green fluorescent protein (GFP) under the control of the human ubiquitn C promoter. Cells were labeled with CD11b+ beads in order to separate monocytic cells from the bone marrow using a magnetic field. Nine month old APP+PS1 transgenic mice received $5 \times 10^6$ GFP+CD11b+ monocytic cells injected into a microvascular port once a week for two months and the mice were sacrificed one day after the last injection.

Group 1 received monocytes that were transfected with a NEP-S-HA plasmid which is a secretory form of the neprilysin plasmid that was modified to delete the membrane binding domain and append a signal peptide triggering secretion. Group 2 served as the untreated control group and provided a baseline for immunohistochemical measurements. Fluorescent immunostaining for GFP and anti-HA qualitatively demonstrated that the monocytes had been transfected with neprilysin and had migrated to the brain in the vicinity of the plaques. Significant decreases in Aβ staining between the treated mice and the control group. There were also decreases in Congo red staining between the treated and control group. Putting monocytes together with an amyloid degrading enzyme such as neprilysin offers a powerful novel therapeutic tool for the treatment of Alzheimer's disease. To test the efficacy of the inventive method for the treatment of neurodegenerative diseases, the inventors purified CD11b+ bone marrow monocytes from donor mice ubiquitously expressing a GFP marker using magnetic cell sorting (see Examples, below). Cells were injected into recipient mice using either intracardiac puncture for single injections, or subcutaneous vascular ports inserted into the jugular vein for repeated injections. In all cases the inventors injected $5 \times 10^6$ cells in a volume of 100 μl. In FIG. 1a, blood was collected at multiple times from 5 minutes to 24 hours after a single injection. The inventors found that the injected monocytes cleared rapidly from the circulation with a half life of 90 minutes. Virtually all injected monocytes were cleared by 24 hours after the injection.

To identify if the injected monocytes migrated to the CNS, the inventors compared the tissue distribution of monocytes after the infusion in both nontransgenic mice and mice with amyloid deposits in their brain (16 month old APP+PS1 transgenic mice; Holcomb et al, 1998). Following exsanguination with saline, the numbers of GFP labeled cells in liver, spleen, lung and brain were estimated at 1, 3 and 7 days both by flow cytometry and by histological cell counts using stereology (FIGS. 1b and 1c). Nontransgenic mice had few GFP labeled cells in brain measured either by flow cytometry or stereology (FIGS. 1d and 1e), yet APP+PS1 transgenic mouse brain had concentrations of GFP labeled cells in the same range as peripheral organs. In most peripheral organs (FIGS. 1f-h), the migration of labeled monocytes in the transgenic and nontransgenic mice were comparable, with the exception of the liver where slightly less infiltration was detected in transgenic mice, possibly due to increased competition for the circulating cells by the brain tissue. In all tissues, the half life of the labeled cells found within organs as resident macrophages was several days, with few cells detected one week after the injection. In the brain, the presence of amyloid deposits greatly enhanced the infiltration of monocytes into the CNS.

Figure 2:
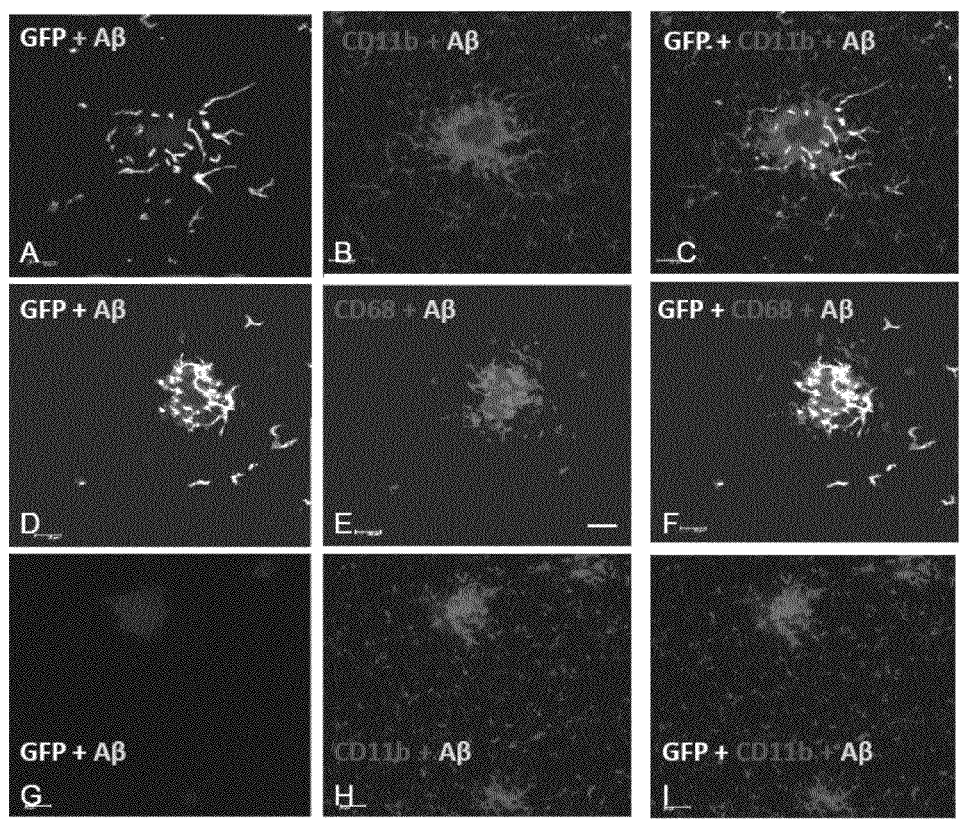
FIG. 2 shows GFP positive monocytes concentrate near plaques in APP+PS1 transgenic animals and exhibit microglial/macrophage phenotype. Imaging of GFP-positive cells was performed using confocal microscopy. Brain sections from APP+PS1 mice collected 1 day after the last of 16 twice weekly injections were stained with fluorescent markers to detect the location and phenotype of the injected monocytes and amyloid plaques. Almost all GFP cells colocalized with CD11b (FIG. 2a-c). Ameboid GFP cells also expressed the phagocyte marker CD68 (2d-f), while ramified GFP cells rarely expressed this marker. No GFP positive cells were detected in uninjected control mice, although CD11b positive cells were comparable to those in the mice injected with GFP monocytes (2g-i). Pictures were taken at 63× and scale bar=20 µm.

Within the brain the inventors found the GFP labeled cells homed to the immediate vicinity of the compacted amyloid deposits. The majority of plaques in mice administered twice weekly injections for 2 month had multiple GFP labeled cells in the surrounding region. Virtually all of these GFP cells expressed CD11b (FIG. 2a-c). A second marker, CD68, expressed by phagocytic cells, labeled largely those microglia/macrophages in the immediate vicinity of the plaque (FIG. 2e). Double labeling studies found that some, but not all of the GFP labeled cells co-expressed CD68, in particular those GFP cells that were less ramified tended to co-express this marker (FIG. 2f). No GFP labeled cells could be found in APP+PS1 mice that were not injected with labeled monocytes (FIG. 2g-i).

These results show that peripheral monocytes migrate to sites of neurodegeneration within the brain. At least in this instance, the migration is not induced by irradiation damage to the CNS (or other tissues). Moreover, these studies may be the first to estimate the half lives of the circulating monocytes and the half lives of the infiltrating monocytes in this manner, both of which were shorter than anticipated. The injected monocytes increases the numbers in blood by at least a factor of 2. Hence the elevated monocyte concentration may contribute to the high degree of labeling the inventors find in the CNS of transgenic mice. However, it is unlikely that mechanical or chemical aspects of the intravenous injection (5% of blood volume) account for the CNS infiltration observed, as very few cells entered the brains of nontransgenic mice. The inventors interpret these data as indicating that circulating monocytes contribute a significant fraction of the activated myeloid cells in the vicinity of compacted amyloid plaques.

Secreted Form of Neprilysin

Neprilysin is an ectoprotease that may be the primary enzyme responsible for Aβ degradation within the brain (Iwata et al, 2001; Man et al, 2003; Leissring et al, 2003; Hemming et al, 2007). Neprilysin is also known as membrane metalloendopeptidase, neutral endopeptidase (NEP), CD10, and common acute lymphoblastic leukemia antigen (CALLA), is a zinc-dependent metalloprotease enzyme that degrades a number of small secreted peptides, most notably the amyloid beta peptide whose abnormal misfolding and aggregation in neural tissue has been implicated as a cause of AD. Synthesized as a membrane-bound protein, the neprilysin ectodomain is released into the extracellular domain after it has been transported from the Golgi apparatus to the cell surface.

To enhance the likelihood this enzyme would reach amyloid deposits from transfected microglia, the inventors engineered a secreted form of the enzyme (NEP-s) by deleting the transmembrane domain and substituting the signal peptide for glial derived neurotrophic factor. The inventors further appended a haemagluttinin tag to the C terminal of the enzyme. As a control gene, the inventors transfected cells with a mutant form of neprilysin containing a single amino acid substitution (E585V) known to inhibit enzyme activity (NEP-m). For gene therapy studies, the inventors isolated the CD11b+ monocytes from the bone marrow of GFP donor mice and transfected them by electroporation. The inventors obtained a 54% transfection efficiency measured by flow cytometry. Cells were then injected into the jugular vein of 9 month old APP+PS1 mice twice weekly using a subcutaneous port. Tissues were collected 2 month later when the mice were 11 month of age. In addition to the mice injected with NEP-s and NEP-m monocytes, the inventors also collected tissue from 11 month old mice that were untreated and from 9 month old untreated APP+PS1 mice to assess the degree of amyloid deposition when the treatment was initiated.

Figure 3:
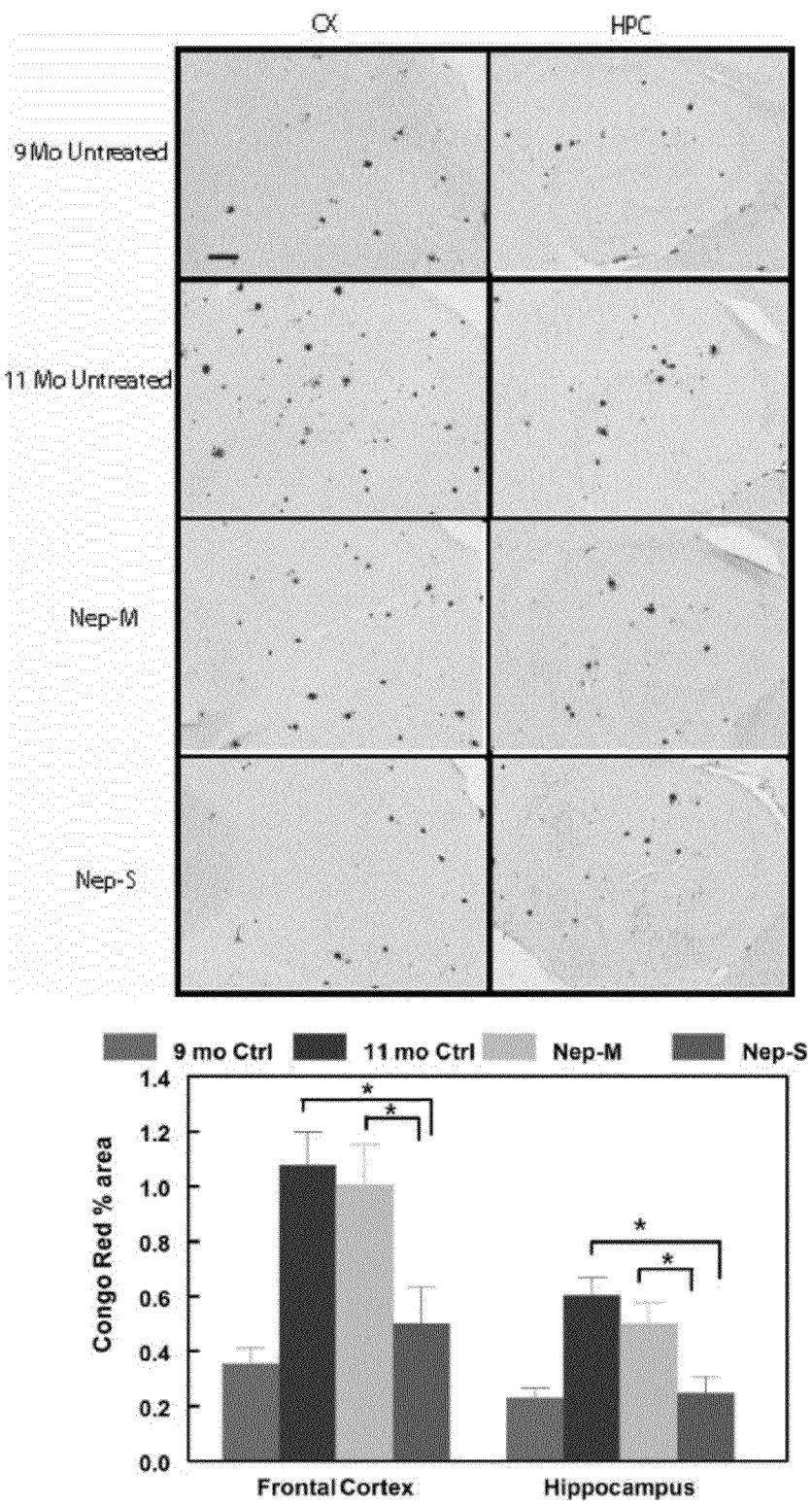
FIG. 3 shows that congophilic amyloid deposition is blocked in APP+PS1 mice infused with GFP monocytes transfected with NEP-s but not NEP-m. Brain sections harvested 1 day after the last infusion were stained with Congo red to estimate the amount of compacted fibrillar plaques. Representative micrographs of staining from frontal cortex (panels on left) or hippocampus (panels on right) are shown for each of the 4 treatment conditions (indicated to the left of each pair of micrographs). The bottom panel shows quantification of percent area of total Congo red staining in the frontal cortex and hippocampus. Sample size pre group=7-9. Statistical analysis was performed using one-way ANOVA with Fisher's LSD multiple comparison test. Brackets between bars signify statistical significance (p<0.05). Values are mean±SEM (standard error of mean). Magnification=40×. Scale bar=120 µm for all panels.

In untreated APP+PS1 mice, there was a dramatic increase in the amyloid load detected with Congo red staining between 9 and 11 month, indicating this was an accelerating phase of amyloid deposition in this model (FIG. 3). Treatment of the mice with NEP-s transfected monocytes completely blocked the increase in amyloid deposition found between 9 and 11 month in these mice. However, treatment with monocytes transfected with the inactive form of the enzyme, NEP-m, showed the same degree of amyloid deposition as the untreated animals.

Figure 4:
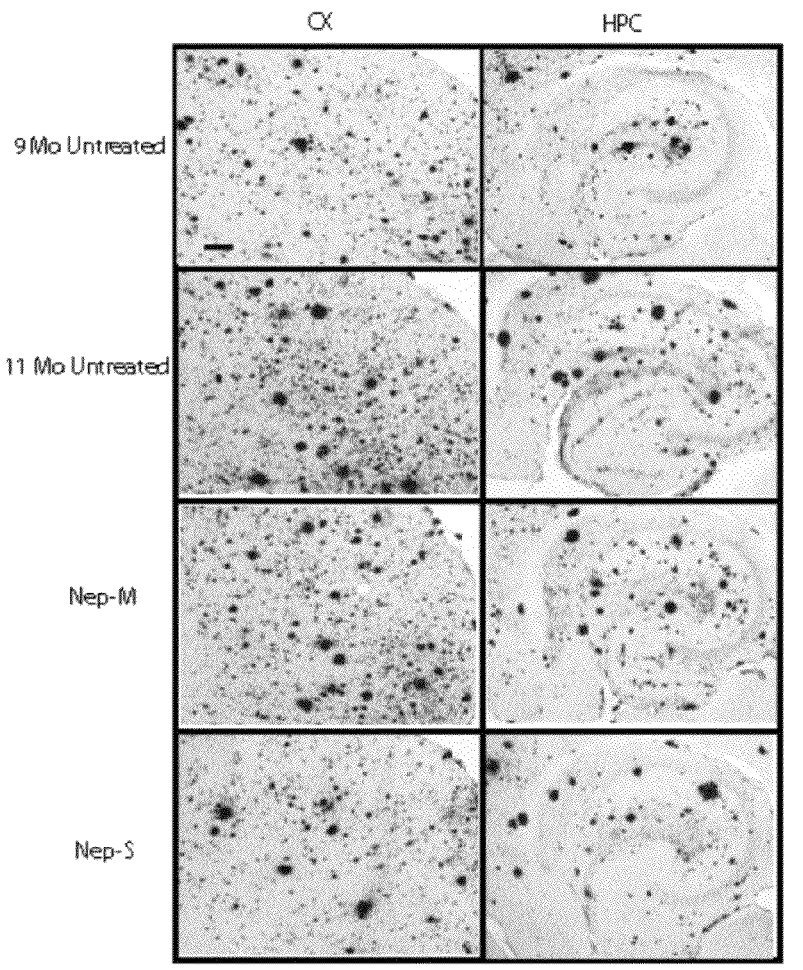
FIG. 4 shows that immunohistochemical Aβ deposition is blocked in APP+PS1 mice infused with GFP monocytes transfected with NEP-s but not NEP-m. Brain sections harvested one day after the last infusion were stained with antibody against Aβ to estimate the amount of diffuse and compacted Aβ deposition. Representative micrographs of staining from frontal cortex (panels on left) or hippocampus (panels on right) are shown for each of the 4 treatment conditions (indicated to the left of each pair of micrographs). The bottom panel shows quantification of percent area of Aβ immunostaining in the frontal cortex and hippocampus. Sample size per group=7-9. Statistical analysis was performed using one-way ANOVA with Fisher's LSD multiple comparison test. Brackets between bars signify statistical significance (p<0.05). Values are mean±SEM (standard error of mean). Magnification=40×. Scale bar=120 µm for all panels.
Figure 4:
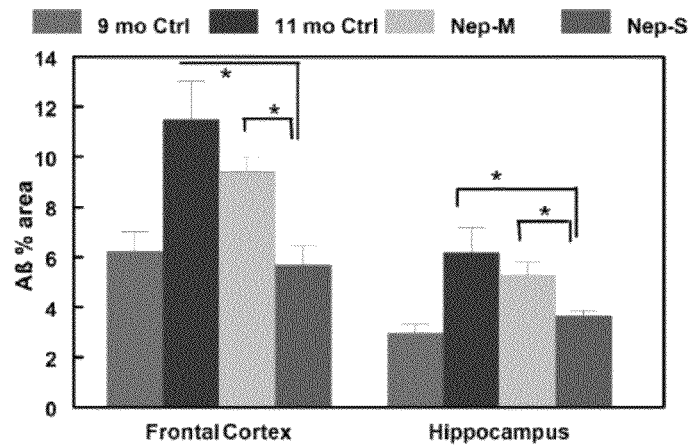

When amyloid loads were measured with a polyclonal antibody to Aβ, a similar 2 fold rise in Aβ deposition was obtained between 9 and 11 month of age (FIG. 4). Again, this elevation was abrogated by the administration of monocytes containing NEP-s, but not NEP-m. There is a trend in the results for the administration of the monocytes with the inactive NEP-m to have less Aβ immunostaining than untreated ice, but this was not statistically significant unless the 9 month control group was excluded from the analysis. Nonetheless, this observation suggests some minor benefit of excess circulating monocytes in slowing Aβ deposition.

These results are the first demonstration that circulating monocytes can be used to deliver therapeutic genes to the CNS. The effect of the monocytes transfected with NEP-s cannot be simply due to increasing the monocyte population as the NEP-m transfected cells had minimal effects on amyloid deposition. Moreover, by measuring the amyloid loads at the beginning of the experiment, the inventors demonstrated that the NEP-s activity totally prevented further amyloid deposition. Few studies have included this control group, and those that have show only slowing of deposition rather than total prevention (J. D. Best et al., 2007). The APP+PS1 mouse is an aggressive model of amyloid deposition, with first deposits around 3-4 month of age and loads at least 3 times greater than the parental single transgenic APP (Tg2576) mouse at most ages. Hence the inventors anticipate that other models, and presumably AD patients, could benefit from even less exposure to the therapeutic gene than that administered here.

EXAMPLES

Mice

Double transgenic APP+PS1 mice that are a cross between the mAPP transgenic line Tg2576 (Hsiao, et al. 1996) and the mPS1 transgenic line 5.1 (Duff et al, 1996). This breeding produces both APP+PS1 mice and nontransgenic mice (littermates) used in this study. The GFP transgenic mouse model for bone marrow donors were from Jackson laboratory C57BL/6-Tg(UBC-GFP)30Scha/J[Stock #004353]. These transgenic mice express the green fluorescent protein (GFP) under the direction of the human ubiquitin C promoter. Sixteen month old transgenic and non transgenic mice were used for the single injection time course study and 9 month old APP+PS1 mice were used for the two month multiple injection study. All mice were bred and maintained in the inventor's animal facility according to institutional guidelines.

Adoptive Transfer of Monocytes

Transgenic GFP mice were overdosed with pentobarbital. The femurs and tibias were removed aseptically and bone marrow was flushed from the bone using a 25 G ⅝ gage needle attached to a syringe. Cells were collected by centrifugation for 5 minutes at 300×g (4° C.). CD11b+ cells were separated using immunomagnetic cell depletion using MACS technology (Miltenyi Biotec, Bergisch Gladbach, Germany). 5×10⁶ freshly isolated CD11b+(GFP) cells were then resuspended in 100 μl saline and injected into the left heart ventricle for the single injection time course studies.

Implantation of Microvascular Port

The microvascular ports (Kent Scientific) are 9×9×3 mm polyurethane ports that were placed subcutaneously in the nape of the neck of a mouse and are connected via catheter to the right jugular vein. A skin incision was made over the area of the right jugular, a sterile trocar tunneled to the soft tissue between the scapula and an incision placed at the tip of the trocar. The vessel was dissected free from surrounding tissue. A proximal and distal ligature were placed around the vessel. The distal ligature was closed, and a venotomy was performed and the catheter advanced into the jugular vein 5 mm The proximal suture was placed around the catheter and secured. A subcutaneous pocket was be made between the scapulae, and the port was placed into the pocket. Both incisions were closed with suture. The catheter was flushed with 100 unit per ml heparin in saline solution, approximately three times the dead space of catheter (30 μl). On the day of injection, mice were anesthetized with isoflurane, the catheter was cleared by inserting a 27 g needle through the skin into the port and injecting 30 μl of 100 U/ml heparin in saline, followed by 100 μl of monocyte cell suspension, followed by another 30 μl of the heparin solution.

Blood

Mice were anesthetized with isoflurane and 1 mL of blood was drawn from each mouse via cardiac puncture. 10 ml of RBC lysis buffer was immediately added to the blood and incubated for 5 minutes. To stop the lysis reaction 30 ml of 1×PBS was added the cells were centrifuged at 300×g at 4° C. for 10 minutes. Cells were resuspended in PBS and evaluated by flow cytometry analysis.

Tissue Collection and Histochemical Procedures

On the day of sacrifice, mice were overdosed with pentobarbital (100 mg/kg). The brain, spleen, liver and lung were removed, bisected sagittally the right half collected for flow cytometry (see below) and the left half was immersed in freshly prepared 4% paraformaldehyde in 100 mM PO4 buffer (pH 7.4). The organs were postfixed in paraformaldehyde for 24 hours. The brain, liver and spleen tissue were cryoprotected in a series of sucrose solutions, frozen, sectioned in the horizontal plane at 25 μm using a sliding microtome and stored at 4° C. in Dulbecco's phosphate buffered saline for immunocytochemistry and histology. The lung tissue was paraffin embedded before being sectioned using a rotary microtome.

Immunohistochemistry was performed on free floating sections as described in detail previously (Gordon et al, 1997). A series of 8 sections spaced approximately 600 nm apart were incubated with primary antibody overnight at 4° C., then incubated in the biotinylated secondary antibody (2 h) followed by streptavidin-peroxidase. Peroxidase reactions consist of 1.4 mM diaminobenzidine with 0.03% hydrogen peroxide in PBS for 5 minutes.

Single and Multiple Immunofluorescent Labeling:

after incubation with the primary antibody, the free floating sections were incubated for 2 hours with the appropriate fluorophore coupled secondary antibodies [AlexaFluor 594 (1:1500), AlexaFluor 488 (1:1500), AlexaFluor 350 (1:1500) (Molecular Probes, Eugene, Oreg.]. Sections were rinsed in Delbecco's PBS and coverslipped with VECTASHIELD Mounting Medium with DAPI.

Antibodies Used for Immunohistochemistry:

Antibodies used for immunohistochemistry: CD11b (rat monoclonal anti CD11b, Serotec, Raleigh, N.C.); GFP (rabbit monoclonal anti-GFP; Chemicon, Temecula, Calif.), 6E10 (mouse monoclonal; Covance, Emeryville, Calif.); CD68 (rat monoclonal; Serotec, Raleigh, N.C.). haemaglutinin (mouse anti-HA rhodamine; Roche, Indianapolis, Ind.).

Congo red histology was performed using sections mounted on slides and air dried. Rehydrated sections were incubated in an alkaline alcoholic saturated sodium chloride solution (2.5 mM NaOH in 80% alcohol, freshly prepared) for 20 minutes, then incubated in 0.2% Congo red in alkaline alcoholic saturated sodium chloride solution (freshly prepared and filtered) for 30 minutes. Sections were rinsed through three rapid changes of 100% ethanol, cleared through three changes of xylene, then coverslipped with DPX.

Image and Flow Cytometry Analysis

Organs were prepared by enzymatic digestion followed by centrifugation over a percoll gradient. GFP fluorescence intensity was measured using a FACScalibur (BD) flow cytometer and analyzed using CellQuest software.

Immunohistochemistry and Congo red staining were quantified with Image Pro Plus (Media Cybernetics) image software. The software uses hue, saturation and intensity (HSI) to segment objects in the image field. Sample numbers are randomized before the start of the tissue processing, and the code is broken only after the analysis is complete. Data was collected from both frontal cortex and hippocampus. All values obtained from a single mouse were averaged together to represent a single value for that animal. Statistical analysis was performed using ANOVA followed by Fischer's LSD post hoc means comparison test (Statview software from SAS).

Stereology

Stereology analysis was performed as described by M. J. West and H. J. G. Gundersen, Unbiased stereological estimation of the number of neurons in the human hippocampus. J. Comp. Neurol. 296 (1990)

$$N = (\text{Number of cells counted}) \times (1/ssf) \times (1/asf) \times (1/tsf)$$

ssf=the sampling fraction (i.e. a ⅙ series or 1/17). The fraction of the total samples used
asf=area sampling fraction
Tsf=thickness sampling fraction Immunoblotting NEP lysates were loaded on SDS polyacrylamide gel electrophoresis and transferred to a nitrocellulose membrane for Western blot analyses. The blots were washed three times using Tris Buffered Saline with Tween 20 (TBST), incubated in milk solution (TBST with 3% non fat dry milk) for 1 hour, and washed three times with TBST. The blots were incubated in the primary antibody (mouse anti-HA; Roche, Indianapolis, Ind.) in milk solution (dilution 1:1000) overnight, washed 3 times with TBST, incubated with the secondary antibody (rabbit anti-mouse 1:1000, Southern; Birmingham, Ala.) in milk solution (dilution 1:1000) for two hours, and washed three times with TBST. The blots were enhanced with LumiGOLD ECL Western Blot Detection Kit (SignaGen Labs; Gaithersburg, Md.) and visualized on film.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. All publications, to which reference is made above, are incorporated herein by said reference. Now that the invention has been described,

What is claimed is:

1. A method for therapeutic gene delivery to a central nervous system of a patient in need thereof for the treatment of neurodegenerative disease comprising the steps of:
    isolating blood or bone marrow from a suitable donor;
    immunolabeling a plurality of Cd11b+ cells within said blood or bone marrow;
    purifying said plurality of immunolabeled Cd11b+ cells from said blood or bone marrow;
    introducing a vector containing a gene that expresses a protease capable of degrading amyloid peptide into the isolated Cd11b+ cells; and
    administering a therapeutically effective amount of the isolated Cd11b+ cells containing the introduced gene peripherally into the patient without irradiation of the patient or any portion of said patient, wherein the Cd11b+ cells containing the gene infiltrate amyloid plaques in the central nervous system of the patient in need thereof.

2. The method according to claim 1 wherein the introduced gene is selected from the group consisting of neprilysin, insulin degrading enzyme and endothelin converting enzyme.

3. The method according to claim 1 wherein the protease capable of degrading amyloid peptide is secreted from the Cd11b+ cells into the extracellular space thereof.

4. The method according to claim 1 wherein the gene that expresses a protease capable of degrading amyloid peptide is the NEP gene with a deletion in the membrane binding domain.

5. The method according to claim 1 wherein the gene that expresses a protease capable of degrading amyloid peptide is the NEP gene with an appended signal peptide to drive secretion of the modified gene product.

6. The method according to claim 1 wherein the gene that expresses a protease capable of degrading amyloid peptide is the NEP gene with a deletion in the membrane binding domain and an appended signal peptide to drive secretion of the modified gene product.

7. The method of claim 1, wherein the Cd11b+ cells are obtained from the patient.

8. A method of testing the efficacy of a therapeutic gene in a central nervous system of a subject for the treatment of neurodegenerative disease, comprising:
    isolating blood or bone marrow from a suitable donor;
    immunolabeling a plurality of Cd11b+ cells within said blood or bone marrow;
    purifying said plurality of immunolabeled Cd11b+ cells from said blood or bone marrow;
    introducing a vector containing a therapeutic gene into the isolated Cd11b+ cells;
    administering the Cd11b+ cells containing the introduced gene peripherally into the subject without irradiation of the subject or any portion of said subject, wherein the Cd11b+ cells containing the gene infiltrate the loci of neurodegeneration within the central nervous system of the subject;
    detecting the presence of the Cd11b+ cells containing the therapeutic gene at the loci of neurodegeneration;
    determining the therapeutic effect of the product of the therapeutic gene of interest at the loci of neurodegeneration.

9. The method according to claim 8 wherein the vector is introduced into the Cd11b+ cells by transfection of the Cd11b+ with a plasmid containing the therapeutic gene of interest.

10. The method according to claim 8 wherein the therapeutic gene of interest includes a deletion in the membrane binding domain.

11. The method according to claim 8 wherein the therapeutic gene of interest includes an appended signal peptide to drive secretion of the modified gene product.

12. The method according to claim 8 wherein the therapeutic gene of interest includes a deletion in the membrane binding domain and an appended signal peptide to drive secretion of the modified gene product.

13. A method for therapeutic gene delivery to a central nervous system of a subject for the treatment of neurodegenerative disease comprising the steps of:
    isolating a plurality of monocytic cells;
    introducing a vector containing a gene that expresses a protease capable of degrading amyloid peptide into the isolated monocytic cells; and
    administering a therapeutically effective amount of the isolated monocytic cells containing the introduced gene peripherally into the patient without irradiation of the subject or any portion of said subject, wherein the monocytic cells containing the gene infiltrate amyloid plaques in the central nervous system of the patient in need thereof.

14. The method according to claim 13, wherein the step of isolating the plurality of monocytic cells includes the steps of:
- isolating blood or bone marrow from a suitable donor;
- immunolabeling said plurality of monocytic cells within said blood or bone marrow; and
- purifying said plurality of immunolabeled Cd11b+ cells from said blood or bone marrow.

15. The method according to claim 13, wherein the step of isolating the plurality of monocytic cells includes density gradient centrifugation.

16. The method according to claim 13, wherein the plurality of monocytic cells is a plurality of Cd11b+ cells.

* * * * *

UNITED STATES PATENT AND TRADEMARK OFFICE
CERTIFICATE OF CORRECTION

Page 1 of 1

PATENT NO. : 8,518,391 B1
APPLICATION NO. : 12/610815
DATED : August 27, 2013
INVENTOR(S) : Dave Morgan It is certified that error appears in the above-identified patent and that said Letters Patent is hereby corrected as shown below:

In the Specification

Column 1, lines 15-18 should read

-- This invention was made with government support under Grant Numbers AG025509 and AG015490 awarded by the National Institutes of Health. The government has certain rights in the invention. --

Signed and Sealed this
First Day of April, 2014

Michelle K. Lee
*Deputy Director of the United States Patent and Trademark Office*